United States Patent [19]

Martinell et al.

[11] Patent Number: 5,914,451
[45] Date of Patent: Jun. 22, 1999

[54] EFFICIENCY SOYBEAN TRANSFORMATION PROTOCOL

[75] Inventors: Brian Martinell, Madison; Lori A. Julson, Lake Mills, both of Wis.; Maud A. W. Hinchee, Wildwood; Dannette Connor-Ward, St. Charles, both of Mo.; Dennis McCabe, Middleton; Carl Emler, Mt Horeb, both of Wis.

[73] Assignee: Monsanto Company, St. Louis, Mo.

[21] Appl. No.: 09/056,073

[22] Filed: Apr. 6, 1998

[51] Int. Cl.$^6$ ............... A01H 5/00; A01H 1/04; C12N 5/04; C12N 15/82
[52] U.S. Cl. ............ 800/300; 435/415; 435/418; 435/419; 435/426; 435/468; 435/470; 435/430; 435/431; 800/278; 800/293; 800/312
[58] Field of Search ............... 435/172.3, 419, 435/410, 415, 418, 420, 426, 430, 431, 468, 470; 800/278, 293, 295, 298, 300, 312

[56] References Cited

U.S. PATENT DOCUMENTS

| | | | |
|---|---|---|---|
| 5,015,580 | 5/1991 | Christou et al. | 435/172.3 |
| 5,416,011 | 5/1995 | Hinchee et al. | 435/172.3 |
| 5,463,175 | 10/1995 | Barry et al. | 800/205 |
| 5,503,998 | 4/1996 | Christou et al. | 435/172.3 |
| 5,569,834 | 10/1996 | Hinchee et al. | 800/205 |
| 5,633,435 | 5/1997 | Barry et al. | 800/205 |

FOREIGN PATENT DOCUMENTS

| | | |
|---|---|---|
| 0 218 571 A2 | 4/1987 | European Pat. Off. . |
| 0 301 749 A2 | 2/1989 | European Pat. Off. . |
| 0 444 882 A2 | 2/1991 | European Pat. Off. ........ C12N 15/82 |
| 0 430 511 A1 | 6/1991 | European Pat. Off. . |
| 0 444 882 A2 | 9/1991 | European Pat. Off. . |

OTHER PUBLICATIONS

Barwale et al, Planta, vol. 167, pp. 473–481, 1986.

Christou et al., "Stable Transformation of Soybean Callus by DNA–Coated Gold Particles", *Plant Physiology* 87:671–674 (1988).

Pang et al., "An Improved Green Fluorescent Protein Gene as a Vital Marker in Plants", *Plant Physiology* 112:893–900 (1996).

*Primary Examiner*—David T. Fox
*Assistant Examiner*—Ashwin D. Mehta
*Attorney, Agent, or Firm*—Quarles & Brady LLP

[57] ABSTRACT

A transformation protocol is described for the particle mediated transformation of soybean. This protocol is based on gene delivery into the growing meristem of a soybean embryo. Prior transformation protocols based on meristematic gene delivery in soybean did not depend on selection due to difficulties in using selection agents in differentiated tissue in soybean. It has been found that a post bombardment culture with glyphosate selection can dramatically increase the efficiency of such a transformation protocol.

12 Claims, No Drawings

EFFICIENCY SOYBEAN TRANSFORMATION PROTOCOL

CROSS-REFERENCE TO RELATED APPLICATIONS

Not applicable.

STATEMENT REGARDING FEDERALLY SPONSORED RESEARCH

Not applicable.

BACKGROUND TO THE INVENTION

Modern science of genetic engineering or biotechnology has provided a number of useful techniques for the improvement of crop plants. Many of these improvements are based on the genetic engineering of plants which involves the transfer of genes of diverse origins into the inheritable germ line of crop plants such that those genes can then be readily bred into or among elite lines of those plants for use in modern agriculture. There are a number of techniques available for the introduction of foreign genes into plants, a process known as genetic engineering, or plant transformation. In general, the techniques for delivery of the genes into plants are independent of the transferred genes, and any technique which has been worked out for a plant species may be used to deliver any particular gene of interest into that plant. Because the cultivation techniques for different plants are quite different from each other, and because transformation techniques generally require intense laboratory cultivation of transformed plant tissue, transformation processes are often species specific and the specific transformation protocols which are most efficiently used with one species of plants often do not work as well with other species of plants.

Most plant transformation techniques rely on the introduction of foreign genes into individual cells of tissue of that plant species maintained in a tissue culture. For example, the most common plant transformation technique in dicot plants is based on the ability of the bacterium *Agrobacterium tumefaciens* to transfer a part of its DNA from the bacterium into the genome of individual dicot plant cells in culture. Typically the foreign gene construction which is transferred into the plant cell includes a gene of interest, which is desired to be introduced into the plant germ line, in tandem with a selectable marker which confers upon the transformed plant cell resistance to a chemical selection agent. In the case of Agrobacterium mediated transformation, the transformation is often performed on callus culture, which is a form of undifferentiated plant cell proliferating in tissue culture. The transformation protocol then typically requires the application of the selection agent to the plant callus tissue which contains some transformed cells therein. The purpose of the selectable marker and the selection agent gene is to separate the cells containing the introduced DNA from those cells which have not been transformed, the separation being performed by killing all or substantially all of the non-transformed cells. Such techniques are widely used for Agrobacterium mediated transformation of a wide variety of dicot species.

For a variety of reasons, these techniques do not work well with all plants, even dicot plant species. For soybean, one early transformation technique was developed which resulted in large numbers of transgenic soybean plants, the technique being based on the approach of particle-mediated gene delivery. In a particle-mediated gene delivery process, the DNA to be inserted into the plant cells is coated onto small carrier particles which are then physically accelerated into tissues of the plant. The carrier particles are very small in relation to the cells of the plant so they actually deliver the genetic material into cells of the plant without killing those cells. Particle-mediated gene delivery can be practiced either on cells of culture or upon actually growing differentiated plant tissue. U.S. Pat. No. 5,015,580 describes some of the first efforts to create transgenic soybean plants through the use of particle-mediated transformation techniques.

The technique developed in the above-identified patent was further refined in the process described in U.S. Pat. No. 5,503,998, describing an improved transformation protocol useful for soybean as well as other plants. In that process, no selection agent is used. The reason that a selectable marker was not useful or used in that process was that the process was based upon the transformation of a few number of cells contained in the growing meristem of an immature embryo of a soybean plant. It was difficult to arrive at a level of application of a selection agent for the then commonly used selectable markers that would permit the growing meristem to still grow, yet still prove toxic to most of the non-transformed cells. Therefore, in the absence of a selectable marker, a different system was utilized for soybean created through the process described in U.S. Pat. No. 5,503,998. That process relied instead on an easily detectable marker, referred to as a screenable marker, which was embodied by the gene beta-glucuronidase or GUS, which could easily be detected by a convenient calorimetric assay. In this process, particle mediated gene delivery was used to introduce a foreign genetic construction into the meristem of an immature embryo which was then induced to directly produce soybean shoots. This process produced large numbers of small shoots created from putatively transformed immature embryos. The majority of the shoots so created were not transgenic. However, the availability of an easily detectable screenable marker, and the relative ease with which large numbers of shoots could be assayed for expression of the selectable marker gene made it practical, and in fact, economic, to simply create large numbers of shoots and look for the rare event in which a transformed shoot was identified. This process enabled the ready creation of large numbers of germ line transgenic plants without the use of a selectable marker.

However, it is always desired to improve the efficiency of any transformation protocol. Thus, the incorporation of a method for improving the efficiency of the method described in the identified US patent would be advantageous. One way to increase the efficiency would be to find a selectable marker that does in fact work with the embryonic transformation system described therein.

A different approach to the transformation of soybean was based on the use of the bacteria *Agrobacterium tumefaciens* to deliver genes into individual plant cells. U.S. Pat. Nos. 5,416,011 and 5,569,834 describe a soybean transformation system based on Agrobacterium-mediated gene delivery to cotyledonary cells of soybean. This system makes use of an antibiotic selectable marker system, which was made to work with this transformation approach.

One herbicide that has received considerable attention as a candidate for use in the development of genetically engineered plants is N-phosphonomethyl-glycine, or glyphosate. Glyphosate inhibits 3-enoylpyruvylshikimate-5-phosphate synthase (EPSP synthase), an enzyme in the shikimic acid pathway. The shikimic acid pathway is a biosynthetic pathway of plants and bacteria in which aromatic amino acids, plant hormones, and vitamins are produced. EPSP synthase catalyzes the conversion of phosphoenolpyruvic acid (PEP) and 3-phosphoshikimic acid to 5-enolpyruvyl-3-phosphoshikimic acid (EPSP).

Glyphosate is an herbicide that is not known to have any adverse environmental effects and which is degraded naturally in the environment. However, glyphosate is nonspecific, in that it is generally effective in inhibiting the growth of both crop plants and weeds. Therefore, glyphosate cannot be effectively applied as a weed control agent when glyphosate intolerant crop plants are present.

In addition to allowing improved weed control, the introduction of glyphosate resistance markers into soybean plants has facilitated the development of genetically engineered soybean plants having advantageous qualities (e.g., higher yields, pest resistance, enhanced nutritional value, and improved storage qualities). Soybean resistant to glyphosate herbicide are already receiving wide acceptance in the marketplace.

Glyphosate tolerant plants can be obtained by engineering the plants to produce higher levels of EPSP synthase (Shah et al., *Science* 233:478–481, 1986). U.S. Pat. No. 5,633,435, which is hereby incorporated by reference herein, discloses EPSP synthase variants, each of which has a reduced $K_i$ for glyphosate, a low $K_m$ for PEP, and a high EPSP synthase activity. Transgenic plants comprising an expressible gene encoding a glyphosate-tolerant EPSP synthase were found to have increased tolerance for glyphosate-containing herbicides.

Another means by which glyphosate tolerant plants can be obtained is to introduce into plants a gene encoding a protein involved in glyphosate degradation. U.S. Pat. No. 5,463,175, incorporated by reference herein, discloses a gene that encodes glyphosate oxidoreductase (GOX), an enzyme involved in the degradation of glyphosate. Also disclosed are glyphosate tolerant transgenic plants comprising a heterologous glyphosate oxidoreductase gene. The enzyme glyphosate oxidoreductase catalyzes the cleavage of the C—N bond of glyphosate to yield amino methyl phosphonate (AMPA) and glyoxylate. Under aerobic conditions, oxygen is used as a substrate in the reaction. Under anaerobic conditions, other electron carriers such as phenazine methosulfate and ubiquinone serve as electron acceptors. A variant of glyphosate oxidoreductase having a 10-fold lower $K_m$ for glyphosate than wild type glyphosate oxidoreductase and mutants of this variant generated by site specific mutagenesis were also disclosed.

In order for the use of agriculturally useful transgenic plants produced by particle mediated transformation to be economically feasible, it is necessary to obtain germ line transformation of a plant, so that progeny of the plant will also carry the gene of interest. Obtaining transgenic plants that exhibit transient expression of an introduced gene has now become a relatively routine, straightforward procedure. However, obtaining a germ line transformed plant through particle mediated transformation methods currently known to the art is a rare through regularly occurring event.

U.S. Pat. Nos. 5,633,435 and 5,463,175 disclose glyphosate tolerant soybeans obtained by microparticle injection transformation. Although the method involves the introduction of a selectable marker into a plant or plant cell, the transformation process is a labor intensive cell culture method.

Although the method disclosed in U.S. Pat. No. 5,503,998 affords a reduction in the amount of work that must be undertaken to identify a germ line transformation event, identification of germ line transformants remains a very labor-intensive undertaking, requiring large numbers of shoots to be screened. Using this method, the transformation efficiency (expressed as the percentage of germ line transformants obtained per explant subjected to particle bombardment) is only about 0.05%. Therefore, in order to obtain a single germ line transformed plant, one must subject approximately 2000 explants to particle bombardment and screen about 6000–8000 shoots using the tissue-destructive GUS assay.

What is needed in the art is an efficient method for obtaining germ line transformed transgenic soybean plants using glyphosate selection.

BRIEF SUMMARY OF THE INVENTION

The present invention is an efficient method for obtaining germ line transformed soybean plants using glyphosate selection.

It is an object of the present invention to provide a method for obtaining germ line transformed soybean plants that is more efficient, economical, and easier to employ than existing methods.

BRIEF DESCRIPTION OF THE DRAWINGS

Not applicable.

DETAILED DESCRIPTION OF THE INVENTION

The present invention is directed to a protocol for the transformation of foreign genes into the germ line of elite soybean varities. The method is genotype independent and achieves the level of efficiency not achieved before by particle-mediated transformation techniques useful in soybean. This efficiency is obtained, in part, through the utilization of a selectable marker system based upon the use of the herbicide glyphosate. Glyphosate selection turns out to have a particular utility in a transformation protocol of the type described here because of the particular attributes of the herbicide glyphosate. Glyphosate is biologically concentrated by the plant in the growing meristem of the plant. The transformation protocol described in this application is based on the direct transformation of growing meristematic tissue. As such, the transformation technique works in conjunction with the glyphosate, since both concentrate their effects at the meristematic region of the growing plant itself. In this way, escapes, or non-transformed events which survive selection, are minimized and the selection still achieves toxicity to most of the non-transgenic tissues. The overall efficiency achieved in the transformation process is better than can be obtained with other selectable markers in soybean transformation systems based upon differentiated tissue transformation.

It was also discovered in the course of the work described here that glyphosate causes a hormone-like effect on treated soybean shoots. In essence, glyphosate alone is effective to induce multiple shoot formation in treated soybean embryonic axes. This observation led to a hormone free regeneration protocol described below.

Examples of high efficiency, germ line transformation of soybean tissue and regeneration of glyphosate resistant plants from the transformed cells using the method of the present invention are detailed below. Briefly, the method requires that a heterologous DNA construct comprising a plant promoter, a DNA sequence encoding a protein that confers glyphosate tolerance, and a 3' untranslated transcriptional terminator region be provided. Copies of the DNA construct are then coated onto relatively small carrier particles of biologically inert material and accelerated into the cells of soybean meristematic tissue. Following transformation of the meristem, transformants are selected on the basis of glyphosate tolerance. Glyphosate tolerant tissue is regenerated to form plants. Germ line transformants may optionally be verified by glyphosate selection of progeny of a plant regenerated from transformed tissue.

Heterologous DNA constructs are provided that encode a gene or genes expressible in a plant, which confer(s) glyphosate tolerance to a plant comprising the DNA construct in its genome. The DNA constructs comprise a plant promoter operably connected to a DNA coding region encoding a protein that confers glyphosate tolerance, and a 3' termination signal. Preferably, the DNA construct encodes an additional gene of interest. For example, the DNA construct may include a gene the expression of which results in increased yields or altered nutrient content in transformed plants. In the examples below, glyphosate tolerant soybean plants expressing GUS or green fluorescent protein (GFP) were obtained from tissue was transformed with DNA constructs that included a GUS gene or a GFP gene. These genes, which can serve as screenable markers, were used in some of the examples described below simply because their phenotypes can be readily detected in the transformed plants. It is reasonable to expect that by using DNA constructs created by standard molecular biological techniques, the present invention may be employed to obtain a soybean plant expressing virtually any other gene.

In an alternative embodiment, the method for obtaining germ line transformed soybean plants involves the cotransformation of two DNA constructs, one of which comprises a glyphosate tolerance marker and the other of which comprises a gene of interest.

A suitable DNA construct comprises a sequence that encodes one or more of the following enzymes: a 5-enolpyruvyl-3-phosphoshikimic acid synthase (EPSP synthase), a glyphosate oxidoreductase (GOX), or a combination of two or more enzymes conferring glyphosate tolerance. The use of other genes conferring glycophosate resistance is also envisioned.

A suitable DNA construct may have a DNA sequence that encodes a wild type EPSP, or an EPSP synthase that has been genetically engineered or mutagenized. Preferably, the DNA sequence encodes an EPSP synthase that is glyphosate tolerant. By "glyphosate tolerant EPSP synthase" it is meant an EPSP synthase having a high $K_i$ for glyphosate and a low $K_m$ for PEP relative to the those parameters of an EPSP synthase from a glyphosate sensitive plant or microorganism. In the examples below, a DNA sequence encoding a glyphosate tolerant EPSP synthase designated CP4 was used in the DNA constructs and was found to confer glyphosate tolerance when introduced alone or together with other glyphosate tolerance genes. The gene encoding CP4 and the CP4 enzyme are described in detail in U.S. Pat. No. 5,633,435 the disclosure of which is hereby incorporated by reference. It is expected that any other EPSP synthase having a low $K_i$ for glyphosate and a high $K_m$ for PEP would function in the practice of the present invention.

A DNA construct may include a wild type glyphosate oxidoreductase gene, or a glyphosate oxidoreductase gene that has been genetically engineered or mutagenized. Preferably, the glyphosate oxidoreductase gene has a low $K_m$ for glyphosate.

There are a number of promoters that are functional in plant cells known to the art, including constitutive promoters of plant pathogenic origin such as the nopaline synthase (NOS) and octopine synthase (OCS) promoters, the cauliflower mosaic virus (CaMV) 19S and 35S promoters, and the figwort mosaic virus (FMV) 35S promoter. In addition, plant promoters which tend to be developmental or tissue specific are now being identified. To create a DNA construct having an expressible glyphosate tolerance gene, one may use any suitable promoter which is known or which may be found to cause transcription of DNA in plant cells. To be suitable for use in the present invention, the promoter should be capable of causing sufficient gene expression to result in the synthesis of an amount of EPSP synthase or glyphosate oxidoreductase effective to render the plant cell or plant substantially tolerant to glyphosate. Preferably, the promoter employed should be capable of promoting expression in meristematic tissue as well as promoting expression in other tissues, because it is known that glyphosate is translocated to and accumulated in meristematic tissue of plants.

In the examples below, the DNA constructs were coated onto gold carrier particles as described in U.S. Pat. No. 5,015,580, which is incorporated by reference herein. It is expected that the present invention could be practiced using other methods for coating carrier particles, and that high density, biologically inert materials other than gold may be successfully employed as DNA carrier particles.

In the examples below, exposed meristematic tissue was used to obtain glyphosate tolerant soybean plants. The use of meristematic tissue was found to greatly enhance the frequency of germ line transformed, glyphosate resistant plants obtained relative to that obtained by the method U.S. Pat. Nos. 5,463,175 and 5,633,435, in which intact embryos served as the target tissue, according to the method of Christou et al. (*Plant Physiol.* 87:671–674, 1988). Glyphosate is known to accumulate in the meristem of soybean plants. The accumulation of glyphosate in the meristem may account for the dramatic noincrease in the incidence of germ line transformants relative to total transformation events obtained when meristematic tissue is used for the transformation and regeneration of glyphosate tolerant soybean plants. While glyphosate selection had been used before to select resistant plants and to select individual undifferentiated resistant cells (as in a callus) there was no experience base for the use of glyphosate to select individual cells from a differentiated growing plant meristem.

Selection on the basis of glyphosate resistance may be the sole basis for identification of recombinant plants, or it may be used in conjunction with other selection or screening methods. In the examples below, glyphosate selection is used alone or in conjunction with screening for GUS expression to identify transgenic plants. Although it is generally preferable to be able to attain efficient selection using a single marker, such as a glyphosate tolerance marker, there may be instances in which it is desirable or necessary to use more than one marker to identify recombinants.

By glyphosate tolerance it is meant the ability of a plant cell or plant transformed with a glyphosate tolerance gene to grow on a medium containing glyphosate at a concentration sufficient to significantly inhibit untransformed cells while allowing the growth of transformed cells. Preferably, the concentration of glyphosate is sufficient to inhibit the growth of at least about 80% of the untransformed explants. The concentration of glyphosate should be sufficient to prevent the survival of untransformed tissue, but not so great as to severely reduce the vigor of transformed plants. In the examples below, glyphosate selection for glyphosate tolerant plant cells was conducted at glyphosate concentrations in the range of from about 0.01 mM to 1.0 mM. In some cases, initial selection was made at a higher concentration of glyphosate, e.g., 0.2 mM glyphosate, and the explant was subsequently transferred to a lower concentration of glyphosate, e.g., 0.075 mM. It was found that concentrations in the 0.025 mM to 0.2 mM range afforded significant inhibition of untransformed tissue without severely affecting the vigor of regenerated transformants. However, it is anticipated that the use of glyphosate at concentrations that fall outside the range used in the examples would also be useful in the present invention.

Other factors that can affect the efficiency of identifying a transformant expressing a resistance gene include the timing and duration of exposure to the selective agent. Therefore, the effect of varying these parameters was also investigated and the results are summarized below. Using the method of the present invention, explants transformed with a glyphosate tolerance gene are most advantageously hosted on a glyphosate-containing media immediately after particle bombardment and/or for several days after bombardment without affecting the transformation efficiency or the number of escapes. The term "escapes" as used herein refers to untransformed explants that are not capable of being distinguished from transformed explants on the basis of glyphosate selection alone. After a period of post-bombardment selection, it may be advantageous but does not appear to be necessary to remove that glyphosate selection, to lower stress or the growing plant shoots. It has been found that removing selection during the shoot elongation phase and thereafter does not detract from overall process efficiency.

The overall plant transformation protocol may be thought of as consisting of several phases, each with unique media requirements exemplary media are described below. There is a pre-bombardment conditioning phase, the actual particle delivery treatment, the post bombardment culture in which shooting is induced, shoot elongation and then root formation and plant hardening. It has been found that just applying glyphosate selection for a limited time during post-bombardment culture is sufficient to dramatically increase the overall efficiency of the transformation process. Application of glyphosate selection at other phases is not as effective in increasing efficiency.

Transformation efficiency as it is used herein is calculated by determining the percentage of germ line transformants as a function of the number of explants subjected to particle bombardment.

The methods described here are based on direct shoot induction from treated embryonic soybean meristems. While the term "regeneration" is used here to describe the re-creation of a whole plant from such treated meristems, the regeneration process in this context is much less difficult and less arduous than regeneration of whole plants from undifferentiated plant tissue, such as callus tissue or protoplasts. By inducing direct shoot formation from the treated embryonic meristems, differentiated growing shoots are directly and rapidly created which readily grow on many different media into whole soybean plants. The way to making this process work is the direct induction of differentiated shoots from the treated embryonic meristem. it was found in the course of this investigation that glyphosate has a surprising role in this process.

To create multiple independent shoot formation from treated soybean meristems, it was prior practice to use hormone treatments on the treated tissue, notably using BAP. It has been found here that glyphosate itself induces multiple independent shoot formation, obviating the need for the hormone. Indeed, as described in Example 2 below, the omission of the BAP and the reliance on the use of glyphosate alone for both selection and for shoot induction, enables a process that is actually more efficient than one based on hormone-induced shoot formation. Again this is an indication of the unique interaction between this molecule and the growing soybean meristem not occurring with other agents.

In the examples below, the soybean explants were subjected to either one or two particle bombardments, with a four hour interval between the two bombardments. It is reasonably expected that the present invention can be practiced with variations in the number or frequency of bombardments. A transformation method employing a single bombardment or more than two bombardments could be equally useful. The present invention is also intended to encompass a method in which explants are subjected to multiple bombardments separated by a period of time longer or shorter than four hours.

The transformed explants expressing glyphosate tolerance activity are regenerated into whole plants. The choice of methodology for the regeneration step is not critical to the present invention. Any method for regeneration of soybean plants may be employed. The media formulations employed in the development of this method are disclosed in the examples. It is expected that other media suitable for the regeneration of plants would be effective in the practice of the present invention.

The following nonlimiting examples are intended to be purely illustrative.

EXAMPLE 1

Methods and Materials

Media preparation

Media employed in the development of glyphosate resistant soybeans plants were prepared using standard methods known to one of skill in the art. Media formulations may be found in the cited references or in the media Table (Table 5).

Preparation of meristem for transformation by particle bombardment

Embryonic axes were excised from seeds germinated in liquid bean germination medium (BGM) overnight at 20° C. in the dark. The composition of BGM is provided in the Appendix. The primary leaf tissue was carefully removed to exposed the meristematic region. Explants were plated on OR medium perpendicular to the surface, with the meristems oriented away from the medium, and explants were incubated overnight at 15° C. in the dark. OR medium is MS medium, as modified by Barwale et al. (*Planta* 167:473–481, 1986) plus 3 mg/l BAP, 200 mg/l Carbenicillin, 62.5 mg/l Cefotaxime, and 60 mg/l Benomyl. OR medium includes the MS major salts, a 4× concentration of minor elements (as per Murashige and Skoog(1962)), B5 vitamins as per Gamborg et al. (1968), 13.3 $\mu$M BAP, 0.2 $\mu$M NAA, 5.0 $\mu$M thiamine, and 12 mM proline.

Preparation of sheets for particle bombardment

A bead preparation for coating the blasting sheets was prepared as follows. Five $\mu$l DNA (1 mg/ml) was added to 100 $\mu$l of 0.1 M spermidine. The spermidine/DNA solution was transferred to a vessel containing 10 mg of 0.71 $\mu$m beads and vortexed completely. One hundred $\mu$l 10% $CaCl_2$ was added dropwise with continuous vortexing. The mixture was allowed to stand for 10 minutes, during which time precipitation occurred. The supernatant was removed, and the DNA/gold precipitate was resuspended in 20 ml 100% ethanol. A 320 $\mu$l aliquot of the bead preparation was used to coat each blasting sheet. The beads were allowed to settle for approximately 30 seconds, the ethanol was removed, and the sheets were allowed to dry.

Transformation and regeneration of explants

Explants were transferred to target medium (8% low viscosity carboxymethylcellulose, 2% medium viscosity carboxymethylcellulose, 0.4% washed agar) with the meristems facing up. The explants were bombarded twice, with a four hour interval between bombardments, using an electric discharge particle mediated gene delivery instrument. Following particle bombardment, explants were transferred to OR medium and either: 1) maintained on a glyphosate-containing media; 2) transferred to glyphosate-free medium for either three or four days and then transferred to glyphosate-containing media; or 3) exposed to glyphosate for a 14-day period immediately following bombardment. The explants were incubated at 23° C. dark for 2 or 4 days. The explants were then transferred to MSR medium (modified OR medium without NAA hormone plus 0.4 mg/l BAP and 0.04 mg/l IBA) containing from 0 to 0.2 mM glyphosate and placed at 28° C. dark for 7 days. The cultures were acclimated to light by placing the cultures in a shade bank for two days at 28° C., followed by transfer to full light (16 h light/8 h dark) for two days.

After the explants were fully green, they were transferred to woody plant medium (WPM) (McCown & Lloyd, *Proc. International Plant Propagation Soc.*, 30:421, 1981) with the addition of 0.04 mg/l BAP, 200 mg/l Carbenicillin, 60 mg/l Benomyl, and from 0 to 0.2 mM glyphosate. Explants were transferred typically after two weeks to fresh glyphosate-containing WPM until harvest was complete.

Elongated shoots were ready for harvest at five to six weeks after bombardment. Only those shoots having elongated stems (approximately 1 inch in length), full trifoliates, and an active growth tip were harvested. Harvested shoots were transferred to bean rooting medium (BRM; see Media Table) containing from 0 to 0.025 mM glyphosate. Harvests were continued weekly until from three to four harvests were made.

Occasionally, non-transformed shoots emerged in explants that had been held more than two months after transformation or incubated on medium in which the glyphosate has been degraded. It was discovered that non-transformed shoots could be distinguished phenotypically from transformed shoots on the basis of the long, narrow trifoliates, short internodes, and tree-like appearance characteristic of non-transformed shoots. Non-transformed shoots were discarded. The non-discarded explants were transferred to fresh glyphosate-containing WPM.

Rooting typically took place approximately one to four weeks after transfer to BRM. After the root system had developed, the plants were transferred to soil. Plants were maintained in a mist bench for several days in a greenhouse. After the plants had hardened off, they were transferred to standard greenhouse conditions. After a plant developed from three to five trifoliates, it could be tested for the presence of the selectable marker or gene of interest.

Plasmid construction

Plasmids were constructed using standard molecular biological techniques known to one of ordinary skill in the art. The expression cassettes contained withing each construct employed in the examples are summarized in Table 1, with the promoter given first, followed by the gene. The CP4 gene used in constructing the plasmids listed in Table 1 is the CP4syn gene, a synthetic gene coding for CP4 EPSP synthase. The gene was disclosed in U.S. Pat. No. 5,633,435, which is incorporated by reference herein. The GOX gene employed in constructing these plasmids was the GOXsyn gene, a synthetic glyphosate oxidase gene disclosed in U.S. Pat. No. 5,463,175, which is incorporated by reference herein.

TABLE 1

| Plasmid | Features |
| --- | --- |
| wrg4750 | FMV CP4, FMV GUS, NOS NPT |
| pMON17204 | FMV CP4, e35S GUS, FMV GOX, 35S NPTII |
| wrg4818 | FMV CP4, e35S GFP |
| pMON26140 | FMV CP4 ) delivered in |
| WRG5306 | Ubi 3 GUS ) co-transformation |

Screening for the GUS gene in transformed soybean plants

Putative glyphosate tolerant shoots were screened for the expression of GUS using the GUS tissue destructive assay as described in U.S. Pat. No. 5,503,998. The seeds from a glyphosate tolerant R0 plant could be evaluated to identify germ line transformation events by exposing shaved seed section (including a portion of the cotyledon) to indigo-glucuronide (5-bromo-4-chloro-3-indolyl glucuronide) and visualizing the formation of a blue color. The seed from which a section is sliced is capable of germinating and developing into a plant. In this manner, seeds that give rise to R1 germ line transformed plants may be readily identified.

Screening for the GFP gene in transformed soybean plants

The expression of the GFP gene was determined in leaf tissue and/or shaved seed sections using a fluorescent microscope according to the method of Pang, et al. (*Plant Physiol.* 112:893–900, 1996).

Screening for CP4 using ELISA

The presence of the CP4 gene in glyphosate tolerant plants was confirmed by ELISA. The assay is an indirect enzyme-linked immunosorbent antibody sandwich assay that detects the levels of CP4 protein present in plant tissue extracts. The levels of CP4 in plant samples were compared to a purified reference standard of CP4. Briefly, 96-well polystyrene plates were coated with purified rabbit anti-CP4. Plant tissue extract and CP4 reference standards were added to appropriate antibody-coated wells. the plates were then incubated for 30 minute at 37° C. and washed. Horse-radish peroxidase conjugated anti-CP4 antibodies were added to the plates, incubated for 30 minutes at 37° C., and unbound anti-Cp4 antibodies were removed by washing To visualize the presence of an antibody sandwich, TMB substrate was added to each well and the well were examined for the development of a blue color. The action of peroxidase on TMB substrate results in the formation of a soluble blue product. The peroxidase reaction is stopped with 1 M phosphoric acid, which causes the product to turn yellow. The amount of CP4 present in a well is directly related to the intensity of the color in that well.

Results

Transformation efficiency using glyphosate selection

The transformation efficiencies for each trial were determined by calculating the percentage of R1 germ line transformed families obtained per explant subjected to particle bombardment. The transformation efficiencies obtained using this method ranged from 0.89 to 5.21% (Table 2).

Effect of plasmid construct on transformation efficiency

Various plasmid constructs were introduced into soybean explants using particle bombardment. All plasmid constructs contained the CP4 gene under the control of the FMV promoter (Table 1). The pMON17204 construct also contained the FMV GOX expression cassette. The transformation efficiencies obtained using glyphosate selection did not vary significantly with the construct employed (Table 2).

TABLE 2

| Plasmid | Explants | Germ line in R1 Positive R1 Families | Transformation Efficiency (based on R1 Marker) |
| --- | --- | --- | --- |
| wrg4750 | 96 | 1 | 1.04% |
| (FMV CP4, FMV GUS, NOS NPT) | 96 | 3 | 3.13% |
| pMON17204 | 56 | | 1.79% |
| (FMV CP4, e3Ss GUS, FMV GOX, 35s NPT) | 56 | 1 | 1.79% |
| | 112 | 2 | 1.79% |
| | 112 | 3 | 2.68% |
| | 112 | 1 | 0.89% |
| | 56 | 1 | 1.79% |
| | 112 | 2 | 1.79% |
| | 112 | 2 | 1.79% |
| | 56 | 2 | 3.57% |
| | 96 | 2 | 2.08% |
| | 96 | 1 | 1.04% |
| | 96 | 1 | 1.04% |
| wrg 4818 | 100 | 3 | 3.00% |
| (FMV CP4, e35s GFP) | 100 | 4 | 4.00% |
| pMON26140/5306X (FMV CP4 and Ubi 3 GUS) | 4688 | 38 | 0.81% |

Effect of time and duration of glyphosate exposure on transformation efficiency and escapes The timing of glyphosate exposure of soybean explants following particle bombardment did not significantly effect the transformation efficiency. If the timing of glyphosate exposure were to affect transformation efficiency some would have expected that a delay in exposure would increase the transformation efficiency. However, no such effect was observed; consequently, there is no advantage to delaying exposure to glyphosate. The data collected to date does indicate that immediate exposure to glyphosate appears to reduce the number of "escapes" (Table 3). Therefore, in the practice of the present invention it would be preferable to transfer transformed explants to glyphosate-containing medium immediately following particle bombardment.

Incidence of germ line transformants using cotransformation

It was discovered that germ line transformants can be obtained with high frequency (about 0.8% transformation efficiency) using cotransformation of a DNA construct containing a gene of interest and a DNA construct containing an expressible glyphosate marker. (Table 3) A heterologous GUS gene placed under the control of a ubiquitin promoter (Ubi-GUS) was found in about 80% of glyphosate tolerant plants obtained by cotransformation of a construct containing the Ubi-GUS gene and a plasmid containing FMV-CP4.

TABLE 4-continued

| Exp ID # | Explants | Visual phenotype positive Shoots | Efficiency (At Shoot Harvest) |
|---|---|---|---|
| 2241 | 512 | 90 | 18% |
| 2242 | 512 | 67 | 13% |
| 2248 | 512 | 136 | 27% |
| 2249 | 512 | 66 | 13% |

The explants were arranged on targeting plates in arrays of 16 explants and were subjected to a single particle mediate gene delivery event (blast).

The explants were cultured thereafter in the presence of glyphosate but the absence of the phytohormones BAP or

TABLE 3

| Plasmid | Explants | Plants | R0 Elisa CP4+ | R1 Gus/GFP + Families | Transformation Efficiency (based on R1 Gus +) |
|---|---|---|---|---|---|
| wrg4750 (FMV CP4, FMV GUS, NOS NPT) | | | | | |
| exp 31, 0.2 mM Gly, 3 day delay | 96 | 3 | 3/3 | 1/3 | 1.04% |
| exp 31, 0.1 mM Gly, 3 day delay | 96 | 6 | 5/6 | 3/4 | 3.13% |
| pMON17204 (FMV, CP4, e35s GUS, FMV GOX, 35s KAN) | | | | | |
| exp 5, 0.1 mM Gly, Constant | 56 | 9 | no data | 1/9 | 1.79% |
| exp 7, 0.05 mM Gly, Constant | 56 | 8 | no data | 1/8 | 1.79% |
| exp 7, 0.1 mM Gly, 4 day delay | 112 | 6 | no data | 2/6 | 1.79% |
| exp 7, 0.2 mM Gly, 4 day delay | 112 | 6 | no data | 3/4 | 2.68% |
| exp 20, 0.01 mM Gly, 4 day delay | 112 | 6 | no data | 1/6 | 0.89% |
| exp 20, 0.01 mM Gly, Constant | 56 | 5 | no data | 1/5 | 1.79% |
| exp 20, 0.05 mM Gly, 4 day delay | 112 | 7 | no data | 2/7 | 1.79% |
| exp 20, 0.1 mM Gly, 4 day delay | 112 | 3 | no data | 2/3 | 1.79% |
| exp 20, 0.1 mM Gly, Constant | 56 | 3 | no data | 2/3 | 3.57% |
| exp 33, 0.1 mM Gly, 3 day delay | 96 | 3 | 3/3 | 2/2 | 2.08% |
| exp 33, 0.075 mM Gly, 3 day delay | 96 | 5 | 3/5 | 1/5 | 1.04% |
| exp 33, 0.075 mM Gly, Constant | 96 | 3 | 3/3 | 1/2 | 1.04% |
| wrg 4818 (FMV CP4, e35s GFP) | 100 | 8 | 7/7 | 3/3 | 3.00% |
| exp 38, 0.1/0.075 mM Gly, 3 day delay | 100 | 7 | 3/3 | 4/5 | 4.00% |

EXAMPLE 2

Methods and Materials

The media, methods and materials were used as in Example 1 above, except as indicated here below.

Preparation of Sheets for Particle Bombardment

Gold particles (beads) of approximately 1 μm in size were used. After adding $CaCl_2$, precipitation and removal of supernatant, the precipitant was resuspended in 10 ml of 95% ethanol. The DNA coated particles were applied to the carrier sheets at a density of 0.1 mg/cm$^2$.

Transformation and Regeneration

After the embryonic axes were excised and germinated, as described in Example 1, the explants were plated on WPM and stored overnight at 15° C.

TABLE 4

| Exp ID # | Explants | Visual phenotype positive Shoots | Efficiency (At Shoot Harvest) |
|---|---|---|---|
| 2215 | 992 | 294 | 30% |
| 2216 | 624 | 114 | 18% |
| 2228 | 640 | 100 | 16% |
| 2229 | 640 | 241 | 38% |

IBA. The medium used both post-bombardment and through shooting was WPM containing 0.075 mM glyphosate but without BAP. The rooting medium used was as in Example 1 supplemented with 0.500 mM tryptophane, tyrosine, and phenylalanine.

The results are summarized in Table 4.

Results

This protocol has been used in eight production scale replicates, using plasmid pWRG4750. They were screened first on the basis of visual phenotype. Non-transformed, shoots appeared sickly and distinctly less vigorous. The numbers in the column "Visual Phenotype Positive Shoots" were numbers of shoots emerging from treated tissues that appeared to be healthy and glyphosate resistant.

The efficiency at shoot harvest is simply the number of phenotypically positive shoots divided by the number of treated explants. The average efficiency at that stage was 22%.

Total process efficiency depends, of course, on verification of gene expression. The shoots from procedures 2215 and 2216 were screened for gene expression (GUS). From the two experiments, respectively 87% (257) and 89% (101) of the phenotypically positive shoots were also GUS positive. Assuming that these results are typical, total process efficiency to transgenic plants would then be approximately 20%, a highly efficient rate.

TABLE 5

BEAN GERMINATION MEDIUM (BGM 2.5%)

| COMPOUND: | QUANTITY PER LITER |
| --- | --- |
| BT STOCK #1 | 10 ml |
| BT STOCK #2 | 10 ml |
| BT STOCK #3 | 3 ml |
| BT STOCK #4 | 3 ml |
| BT STOCK #5 | 1 ml |
| SUCROSE | 25 g |
| Adjust to pH 5.8. | |
| DISPENSED IN 1 LITER MEDIA BOTTLES, AUTOCLAVED | |

| ADDITIONS PRIOR TO USE: | PER 1L |
| --- | --- |
| CEFOTAXIME (50 mg/ml) | 2.5 ml |
| "ANTILIFE" FUNGICIDE STOCK | 3 ml |

BT STOCK FOR BEAN GERMINATION MEDIUM

Make and store each stock individually. Dissolve each chemic thoroughly in the order listed before adding the next. Adjust volume of each stock accordingly. Store at 4° C.
Bt Stock 1 (1 liter)

| | |
| --- | --- |
| $KNO_3$ | 50.5 g |
| $NH_4NO_3$ | 24.0 g |
| $MgSO_4 7H_2O$ | 49.3 g |
| $KH_2PO_4$ | 2.7 g |

Bt Stock 2 (1 liter)

| | |
| --- | --- |
| $CaCl_2$ $7H_2O$ | 17.6 g |

Bt Stock 3 (1 liter)

| | |
| --- | --- |
| $H_3BO_3$ | 0.62 g |
| $MnSO_4$—$H_2O$ | 1.69 g |
| $ZnSO_4$—$7H_2O$ | 0.86 g |
| KI | 0.083 g |
| $NaMOC_4$—$2H_2O$ | 0.072 g |
| $CaSO_4$—$5H_2O$ | 0.25 ml of 1.0 mg/ml stock |
| $CoCl_4$—$6H_2O$ | 0.25 ml of 1.0 mg/ml stock |

Bt Stock 4 (1 liter)

| | |
| --- | --- |
| $Na_2EDTA$ | 1.116 g |
| $FeSO_4 7H_2O$ | 0.834 g |

Bt Stock 5 (500 mls) Store in a foil wrapped container

| | |
| --- | --- |
| Thiamine-HCl | 0.67 g |
| Nicotinic Acid | 0.25 g |
| Pyridoxine-HCl | 0.41 g |

BEAN ROOTING MEDIUM (BRM)

| COMPOUND: | QUANTITY PER 4L: |
| --- | --- |
| MS SALTS | 8.6 g |
| MYO-INOSITOL | .40 g |
| (Cell Culture Grade) | |
| SBRM VITAMIN STOCK | 8 ml |
| L-CYSTEINE (10 mg/ml) | 40 ml |
| SUCROSE (ULTRA PURE) | 120 g |
| Adjust pH to 5.8. | |
| WASHED AGAR | 32 g |
| ADDITIONS AFTER AUTOCLAVING: | |
| SBRM/TSG HORMONE STOCK | 20.0 mls |

SOY TISSUE CULTURE HORMONE PRE-MIXES

MSR/TSG Pre-mixed Hormones

Use 10.0 mls per liter
Store dark at 4° C.

TABLE 5-continued

| Amount for 1 liter | Amount for 20 liters |
| --- | --- |
| 0.80 ml BAP (0.5 mg/ml) | 16.0 mls BAP (0.5 mg/ml) |
| 0.040 ml IBA (1.0 mg/ml) | 0.80 ml IBA (1.0 mg/ml) |
| 9.16 mls SDW | |

OR/TSG Pre-mixed Hormones

Use 10.0 mls per liter
Store dark at 4° C.

| Amount for 1 liter | Amount for 30 liters |
| --- | --- |
| 6.0 mls BAP (0.5 mg/ml.) | 180.0 mls BAP (0.5 mg/ml) |
| 0.037 ml NAA (1.0 mg/ml) | 1.11 mls NAA (1.0 mg/ml) |
| 3.96 mls SDW | 118.8 mls SDW |

WPM/TSG Pre-mixed Hormones

Use 10.0 mls per liter
Store dark at 4° C.

| Amount for 1 liter | Amount for 50 liters |
| --- | --- |
| 0.080 ml BAP (0.5 mg/ml) | 4.0 mls BAP (0.5 mg/ml) |
| 9.92 ml SDW | 496.0 mls SDW |

SBRM/TSG Pre-mixed Hormones
(Soybean Rooting Medium)

Use 10.0 mls per liter for SBRM
Store dark at. 4° C.
NOTE: Use 5.0 mls per liter
for BRM.

| Amount for 1 liter | Amount for 40 liters |
| --- | --- |
| 6.0 mls IAA (0.033 mg/ml) | 240.0 mls IAA (0.033 mg/ml) |
| 4.0 mls SDW | 160.0 mls SDW |

VITAMIN STOCK FOR SOYBEAN ROOTING MEDIA (1 liter)

| | |
| --- | --- |
| Glycine | 1.0 g |
| Nicotinic Acid | 0.25 g |
| Pyridoxine HCl | 0.25 g |
| Thiamine HCl | 0.05 g |

Dissolve one ingredient at a time, bring to volume, store in foil-covered bottle in refrigerator for no more than one month

3X MINOR MS SALTS STOCK (1 liter)

| | | |
| --- | --- | --- |
| $H_2BO_3$ | 1.86 | g |
| $MNSO_4$—$H_2O$ | 5.07 | g |
| $ZnSO_4$—$7H_2O$ | 2.58 | g |
| KI | 0.249 | g |
| $NaMoO$—$2H_2O$ | 7.5 | μl |
| $CoSO_4$—$5H_2O$ Stock, (1.0 mg/ml) | 7.5 | μl |
| $CoCl_2$-$6H_2O$ Stock (1.0 mg/ml) | 7.5 | μl |

Dissolve one chemical at a time, adjust volume, store in refrigerator.

ANTILIFE FUNGICIDE STOCK (100 mls)

| | | |
| --- | --- | --- |
| BRAVO (75% WP) | 1.0 | g |
| Benomyl (50% OF) | 1.0 | g |
| Captan (50% WP) | 1.0 | g |

Add to 100 mls of sterile distilled water.
Shake well before using.
Store 4° C. dark for no more than one week.

What is claimed is:

1. An efficient method of obtaining germ line-transformed soybean plants using glyphosate selection comprising the steps of:

(a) providing a heterologous DNA construct comprising a promoter functional in plants operably connected to a DNA coding sequence, the coding sequence encoding a protein capable of conferring glyphosate tolerance to a plant cell in which the sequence is expressed, and a 3' termination sequence;

(b) coating copies of the DNA construct onto carrier particles of biologically inert material, the carrier particles being small in size relative to a soybean cell;

(c) accelerating the coated particles into the meristem tissue of a soybean embryo;

(d) inducing shoot formation from the treated meristem tissue by culturing the treated meristem tissue on a culture medium comprising a plant hormone and glyphosate;

(e) culturing the shoots on a suitable shooting medium containing glyphosate at a concentration sufficient to significantly inhibit the growth of untransformed soybean cells to generate glyphosate resistant soybean shoots; and (f) regenerating the shoots of step (e) into genetically transformed soybean plants having increased tolerance to glyphosate herbicide relative to wild type soybean plants.

2. The method of claim 1, wherein there is regeneration media used in step (f) and wherein there is no glyphosate in the regeneration media used in step (f).

3. The method of claim 1, wherein the DNA construct additionally comprises a gene of interest.

4. The method of claim 1 wherein the hormone is BAP.

5. An efficient method of obtaining germ line-transformed soybean plants using glyphosate selection comprising the steps of:

(a) providing a heterologous DNA construct comprising a promoter functional in plants operably connected to a DNA coding sequence, the coding sequence encoding a protein capable of conferring glyphosate tolerance to a plant cell in which the sequence is expressed, and a 3' termination sequence;

(b) coating copies of the DNA construct onto carrier particles of biologically inert material, the carrier particles being small in size relative to a soybean cell;

(c) accelerating the coated particles into the meristem tissue of a soybean embryo;

(d) inducing direct shoot formation from the treated meristem tissue comprising culturing on a plant hormone-free medium containing glyphosate at a concentration sufficient to inhibit the growth of untransformed soybean cells to induce gyphosate resistant shoots;

(e) culturing the shoots on a suitable shooting medium containing glyphosate at a concentration sufficient to significantly inhibit the growth of untransformed soybean cells to generate glyphosate resistant soybean shoots; and (f) regenerating the shoots of step (e) into genetically transformed soybean plants having increased tolerance to glyphosate herbicide relative to wild type soybean plants.

6. The method of claim 1, wherein the DNA construct comprises an EPSP synthase gene.

7. The method of claim 6, wherein the EPSP synthase gene is CP4.

8. The method of claim 6, wherein the DNA construct further comprises a gene encoding an glyphosate oxidoreductase enzyme.

9. The method of claim 1 further comprising the step of comparing the morphological appearance of the shoots as a measure of glyphosate tolerance and discarding before step (f) those shoots having visually abnormal morphological appearance.

10. The method of claim 1 wherein the level of glyphosate used-in step (e) is between 0.01 and 1.0 mM glyphosate in the culture medium.

11. The method of claim 1 wherein the number of transgenic shoots recovered as a percentage of the number of meristems treated is at least 1%.

12. The method of claim 11 wherein the number of transgenic shoots recovered is a percentage of the number of meristems treated is about 20%.

* * * * *